(12) United States Patent
Kawakami (10) Patent No.: US 10,695,335 B2
(45) Date of Patent: Jun. 30, 2020

(54) PATCH PREPARATION

(71) Applicant: Teikoku Seiyaku Co., Ltd., Higashikagawa-shi, Kagawa (JP)

(72) Inventor: Satoshi Kawakami, Higashikagawa (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 444 days.

(21) Appl. No.: 15/123,517

(22) PCT Filed: Feb. 24, 2015

(86) PCT No.: PCT/JP2015/055173
§ 371 (c)(1),
(2) Date: Sep. 2, 2016

(87) PCT Pub. No.: WO2015/133329
PCT Pub. Date: Sep. 11, 2015

(65) Prior Publication Data
US 2016/0367536 A1    Dec. 22, 2016

(30) Foreign Application Priority Data

Mar. 6, 2014  (JP) .................................. 2014-044252

(51) Int. Cl.
*A61F 13/00* (2006.01)
*A61K 31/445* (2006.01)
(Continued)

(52) U.S. Cl.
CPC .......... *A61K 31/445* (2013.01); *A61K 9/7046* (2013.01); *A61K 9/7061* (2013.01); *A61M 37/00* (2013.01)

(58) Field of Classification Search
USPC ........................................................... 602/48
See application file for complete search history.

(56) References Cited

U.S. PATENT DOCUMENTS

| | | | |
|---|---|---|---|
| 5,503,844 A * | 4/1996 | Kwiatek ................ | A61K 9/703 424/434 |
| 8,974,817 B2 * | 3/2015 | Ito ........................ | A61K 9/7061 424/449 |

(Continued)

FOREIGN PATENT DOCUMENTS

| CA | 2719605 A1 * | 10/2009 | ........... A61K 9/7061 |
|---|---|---|---|
| JP | 11-43431 A | 2/1999 | |

(Continued)

OTHER PUBLICATIONS

International Search Report (PCT/ISA/210) issued in PCT Application No. PCT/JP2015/055173 dated May 26, 2015, with English translation (four (4) pages).

(Continued)

Primary Examiner — Kim M Lewis
(74) Attorney, Agent, or Firm — Crowell & Moring LLP (57) ABSTRACT

Provided is a patch preparation that has improved adhesion to an adherend so as to enable a drug, especially, a systemically active drug to be stably and continuously administered over an extended period. The patch preparation has a layered structure comprising a patch layer including an adhesive plaster containing a drug and a patch support, and a cover layer in this order from a side attached to a skin. In the patch preparation, a buffer material is disposed between the patch support of the patch layer and the cover layer, the cover layer has a size covering an area beyond peripheral edges of the patch layer, and a shielding film is further disposed between the cover layer and the buffer material.

5 Claims, 3 Drawing Sheets

(51) Int. Cl.
*A61K 9/70* (2006.01)
*A61M 37/00* (2006.01)

(56) References Cited

U.S. PATENT DOCUMENTS

| | | |
|---|---|---|
| 2009/0291126 A1 | 11/2009 | Iwao et al. |
| 2011/0104215 A1 | 5/2011 | Ito et al. |
| 2011/0104247 A1* | 5/2011 | Ito .................... A61K 9/7061 424/449 |
| 2013/0164495 A1 | 6/2013 | Isoda et al. |

FOREIGN PATENT DOCUMENTS

| | | |
|---|---|---|
| JP | 11-343232 A | 12/1999 |
| JP | 2005-224981 A | 8/2005 |
| JP | 2007-99759 A | 4/2007 |
| JP | 2008-37798 A | 2/2008 |
| WO | WO 2009/119673 A1 | 10/2009 |
| WO | WO 2012/008396 A1 | 1/2012 |

OTHER PUBLICATIONS

Japanese-language Written Opinion (PCT/ISA/237) issued in PCT Application No. PCT/JP2015/055173 dated May 26, 2015 (four (4) pages).
English translation of B1 (JP 11-343232 A previously filed on Sep. 2, 2016) (seven (7) pages).
English translation of B3 (JP 11-43431 A previously filed on Sep. 2, 2016) (thirteen (13) pages).
English translation of B5 (JP 2008-37798 A previously filed on Sep. 2, 2016) (ten (10) pages).
English translation of B7 (JP 2005-224981 A previously filed on Sep. 2, 2016) (seven (7) pages).

* cited by examiner

PATCH PREPARATION

TECHNICAL FIELD

The present invention relates to a patch provided with a layered support having improved adhesion to an adherend.

BACKGROUND ART

In recent years, a patch containing a so-called systemically active drug, such as tulobuterol (bronchial asthma therapeutic agent), fentanyl (persistent cancer pain therapeutic agent), rivastigmine (Alzheimer disease therapeutic agent), and oxybutynin (overactive bladder therapeutic agent), has been commercially available, and used in a clinical setting.

The patch containing the systemically active drug has such characteristics that the constant blood level of the drug can be maintained for an extended period. Therefore, a patch that can be administered once daily and a patch that can be administered for a period as long as one week have been developed.

From the viewpoints of solubility of the drug and a base ingredient, drug releasability from the base ingredient, stable adherence in long-term administration, or the like, most of the patches may be provided as a so-called tape having a base such as an acrylic adhesive, a silicone-based adhesive, and a styrene-isoprene-styrene block copolymer as a main material.

For stable administration of the drug over an extended period, the mixing amount and the crystalline form of the drug in a patch, and an interaction of the drug and the patch base such as actions of the drug and the base ingredient have been conventionally investigated.

On the other hand, the blood level of the drug has been often tried to be stably maintained by enhancing the adhesive force of a patch itself to prevent peeling of the patch from the skin as much as possible. However, the adhesive force to a movable portion of the skin is insufficient. When the adhesive force is excessively enhanced, a pain occurs during peeling from the skin surface. Further, a possibility of causing skin irritation is also pointed out. Therefore, it is difficult that the percutaneous absorption of the drug is stably maintained over an application period only by simply enhancing the adhesive force of a plaster part.

In order to improve the applicability of a patch to the skin, a method of fixing a patch using a cover sheet (Patent Literature 1) and a reservoir-type patch preparation in which a cover sheet and a patch are integrated (Patent Literature 2) have been proposed.

In these patch preparations provided with the cover sheet, the cover sheet itself is not peeled and detached from an application portion of the skin due to a high adhesive force thereof. However, a patch part or a reservoir part cannot follow the movement of the application portion. Thus, the patch cannot be pressure-bonded to the skin. Therefore, stable drug release may not be achieved.

In particular, when in a patch containing a systemically active drug such as tulobuterol and fentanyl, the blood level of the drug cannot be stably maintained, the patch cannot exhibit a clear beneficial effect. Therefore, it is necessary that a whole patch preparation including a cover sheet part is always firmly adhered to the application portion of the skin. However, a patch satisfying these demands has not yet been developed.

PRIOR ART DOCUMENTS

Patent Literature

Patent Literature 1: Japanese Patent Application Laid-Open No. Hei. 11-343232
Patent Literature 2: International Publication No. WO2009/119673

SUMMARY OF THE INVENTION

Problems to be Solved by the Invention

In order to solve the conventional problems, an object of the present invention is to provide a patch preparation capable of stably and continuously administering a drug, and in particular, a systemically active drug, over an extended period.

Means for Solving the Problem

The present inventor has intensively studied to achieve the object, and as a result, found that in a patch preparation that has a layered structure of a patch layer including an adhesive plaster containing a drug and a patch support and a cover layer in this order from a side attached to the skin, when a buffer material is disposed between the patch support and the cover layer, the pressure-bonding property of the adhesive plaster to the skin is improved, and the adhesive plaster is pressure-bonded to the skin with a constant pressure against the movement of the skin caused by motion or the like. The inventor has found that such a patch preparation capable of stable drug release can be provided. Thus, the present invention has been completed.

Specifically, the present invention includes the following basic aspect.
(1) A patch preparation of a layered structure comprising a patch layer including an adhesive plaster containing a drug and a patch support, and a cover layer in this order from a side attached to a skin, wherein a buffer material is disposed between the patch support of the patch layer and the cover layer, and the cover layer has a size covering an area beyond peripheral edges of the patch layer.

More specifically, the present invention is:
(2) the patch preparation described in the above-described (1), wherein a shielding film is further disposed between the cover layer and the buffer material;
(3) the patch described in the above-described (1) or (2), wherein the buffer material is a non-woven fabric;
(4) the patch preparation described in the above-described (2), wherein the shielding film is a polyethylene terephthalate (PET) film; and
(5) the patch preparation described in any one of the above-described (1) to (4), wherein the cover layer has a size of 150 to 250% of a plane area of the patch layer.

Effects of the Invention

The patch preparation of the present invention is a patch preparation of a layered structure comprising a patch layer including an adhesive plaster containing a drug and a patch support, and a cover layer, and in particular, has characteristics in which a buffer material is disposed between the patch support and the cover layer.

When such a buffer material is disposed, a pressure-bonding action of the adhesive plaster (patch layer) to the application portion of a skin by the cover layer is enhanced, the adhesive plaster is pressure-bonded to the application portion of the skin with a constant pressure against the movement of the skin caused by motion or the like, and stable drug release can be achieved.

Therefore, the patch preparation has an advantage in which a constant blood level of the drug can be maintained for an extended period as a patch especially containing a systemically active drug.

EMBODIMENTS FOR CARRYING OUT THE INVENTION

As described above, the present invention is a patch preparation of a layered structure comprising a patch layer including an adhesive plaster containing a drug and a patch support, and a cover layer in this order from a side attached to the skin, and is characterized in that a buffer material is disposed between the patch support of the patch layer and the cover layer, and the cover layer has a size covering an area beyond peripheral edges of the patch layer.

Hereinafter, the patch preparation provided by the present invention will be described in detail on the basis of the drawings.

Figure 1:
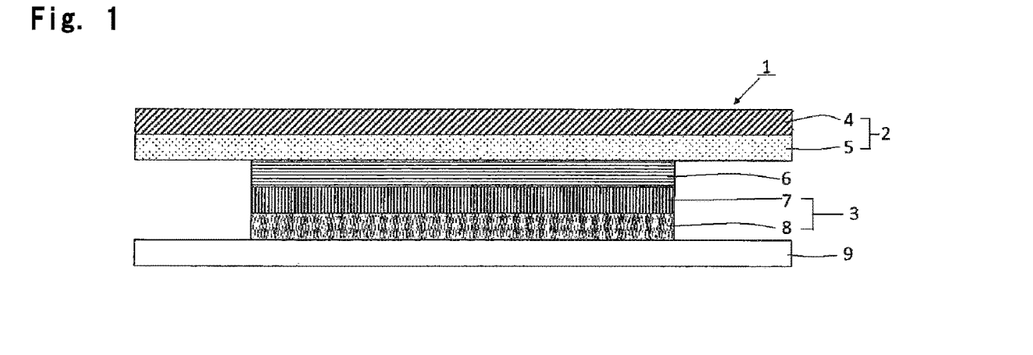
FIG. 1 is a schematic cross-sectional view based on a first embodiment of a patch preparation according to the present invention.

FIG. 1 is a schematic cross-sectional view based on a first embodiment of the patch preparation according to the present invention.

As shown in FIG. 1, a patch preparation 1 of the present invention is a patch preparation of a layered structure comprising a patch layer 3 including an adhesive plaster 8 containing a drug and a patch support 7, and a cover layer 2 in this order from a side attached to a skin. In this patch preparation 1, a buffer material 6 is disposed between the patch support 7 of the patch layer 3 and the cover layer 2, and the cover layer 2 has a size covering an area beyond peripheral edges of the patch layer 3 including the buffer material 6.

Specifically, the patch preparation has a layered structure of the cover layer 2 including a cover support 4 and a cover adhesive 5, and the patch layer 3 including the patch support 7 and the adhesive plaster 8. The buffer material 6 is disposed between the patch support 7 of the patch layer 3 and the cover adhesive 5 of the cover layer 2. Furthermore, the patch preparation is provided with a release liner 9 that is releasably attached to the adhesive plaster 8 and covers the adhesive plaster 8 and others.

In the patch preparation 1 of the present invention, the area of the cover layer 2 is larger than that of the patch layer 3, and the cover layer 2 and the patch layer 3 are layered so that the cover adhesive 5 is left around the patch layer 3.

In this case, it is preferable that the size (area) of the cover layer 2 be 150 to 250% of a plane area of the patch layer 3.

When the size is less than 150%, the attachment force to the application portion of the skin is insufficient. When the size is more than 250%, the size of the attachment portion of the cover layer to the skin is large. Therefore, this is not preferable.

For example, when the patch preparation of the present invention has a rectangle shape of 61 mm×61 mm, as shown from Examples described below, the cover layer may have a size that has a margin of about 5 to 15 mm on four sides of the patch preparation (for example, 71 mm×71 mm).

In the patch preparation of the present invention, the buffer material 6 and the patch support 7 may be configured separately, or may be configured to be integrated, like a laminate support described below. A method of bonding the patch support 7 and the buffer material 6 may be either a dry lamination method or a thermal lamination method. The dry lamination method is preferable.

Figure 2:
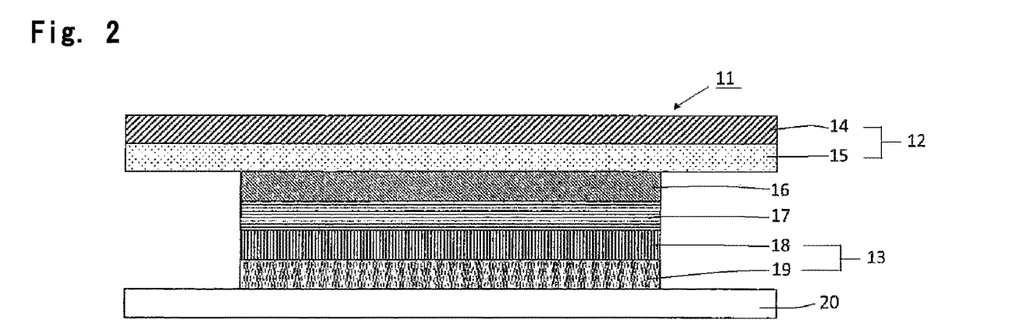
FIG. 2 is a schematic cross-sectional view based on a second embodiment of the patch preparation according to the present invention.
Figure 3:
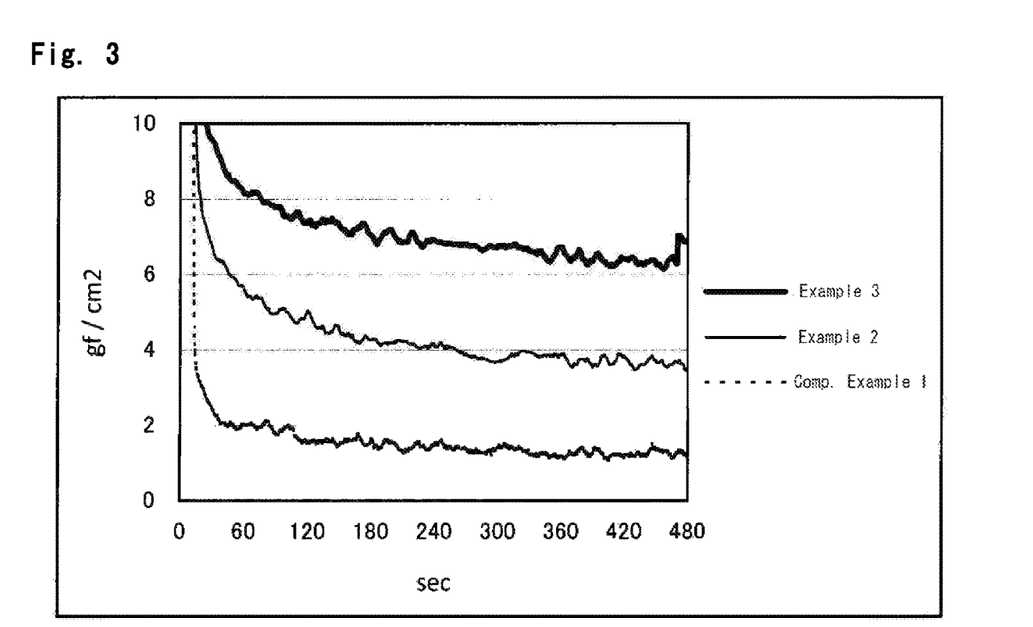
FIG. 3 is a graph showing results of Test Example 1-(1) using patch preparations according to the present invention and a patch preparation of Comparative Example.
Figure 4:
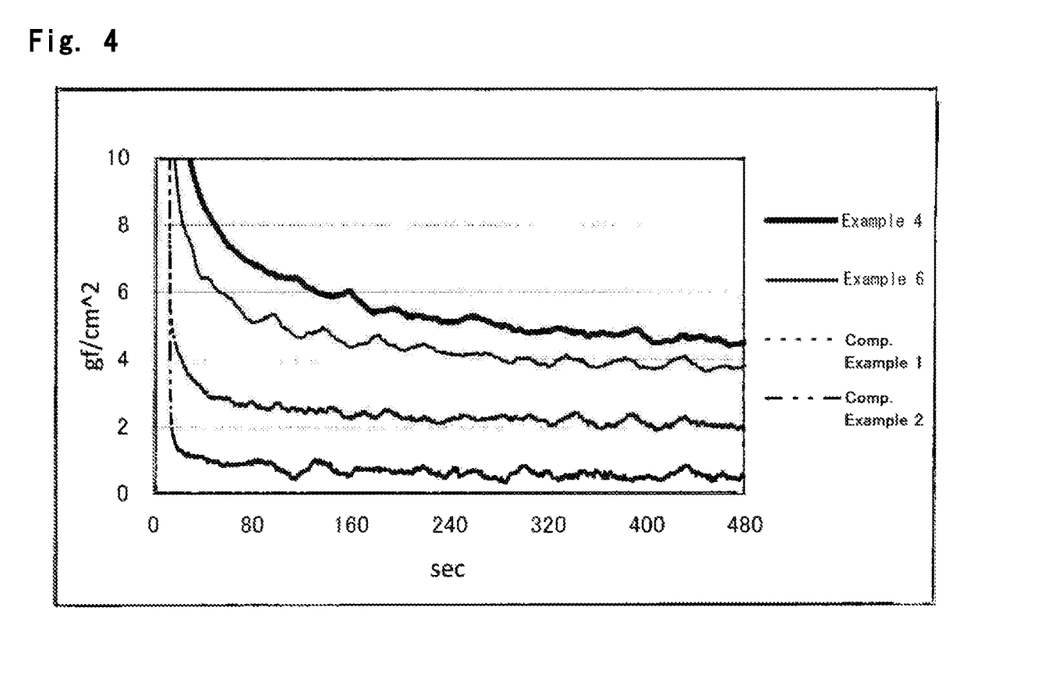
FIG. 4 is a graph showing results of Test Example 1-(2)-A using patch preparations according to the present invention and patch preparations of Comparative Example.
Figure 5:
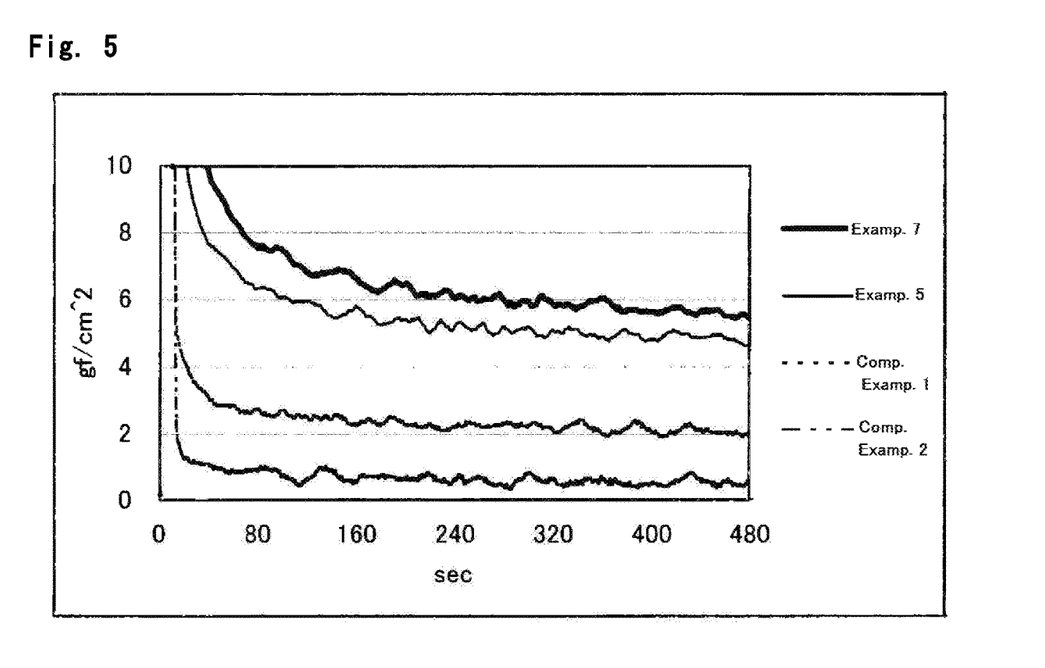
FIG. 5 is a graph showing results of Test Example 1-(2)-B using patch preparations according to the present invention and the patch preparations of Comparative Example.
Figure 6:
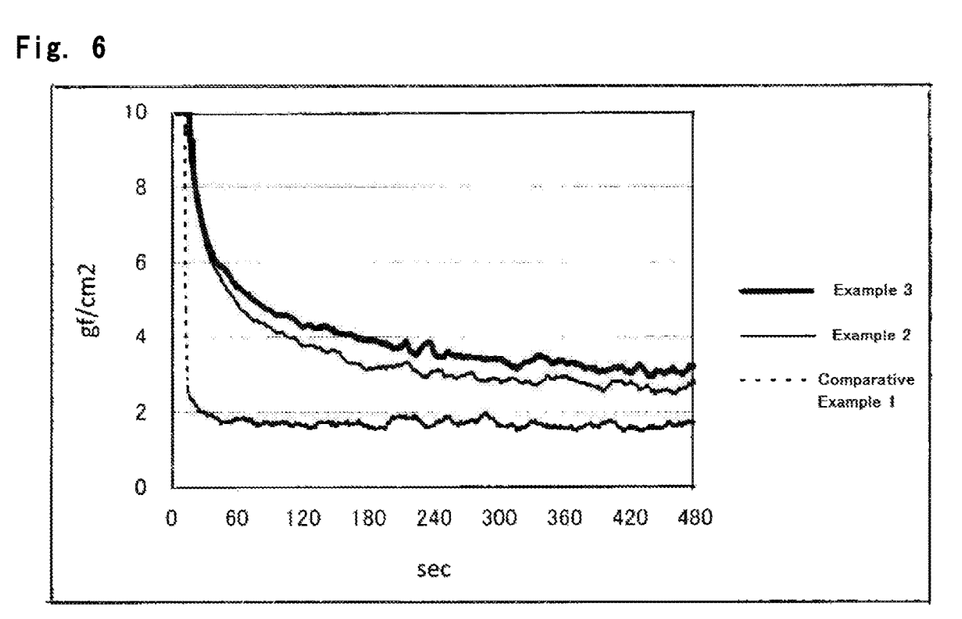
FIG. 6 is a graph showing results of Test Example 1-(3) using the patch preparations according to the present invention and the patch preparation of Comparative Example.

FIG. 2 is a schematic cross-sectional view based on a second embodiment of the patch preparation according to the present invention.

As shown in FIG. 2, a patch preparation 11 of the present invention is a patch preparation of a layered structure comprising a patch layer 13 including an adhesive plaster 19 containing a drug and a patch support 18, and a cover layer 12 in this order from a side attached to a skin. In this patch preparation 11, a buffer material 17 is disposed between the patch support 18 of the patch layer 13 and the cover layer 12, and a shielding film 16 is further disposed therebetween. Furthermore, the cover layer 12 has a size covering an area beyond peripheral edges of the patch layer 13 including the buffer material 17 and the shielding film 16.

Specifically, the patch preparation 11 based on the second embodiment has a layered structure of the cover layer 12 including a cover support 14 and a cover adhesive 15, and the patch layer 13 including the patch support 18 and the adhesive plaster 19. The buffer material 17 is disposed between the patch support 18 of the patch layer 13 and the cover adhesive 15 of the cover layer 12, and the shielding film 16 is further disposed therebetween. Furthermore, the patch preparation is provided with a release liner 20 that is releasably attached to the adhesive plaster 19 to cover the adhesive plaster 19 and others.

In the patch preparation of the second embodiment, the area of the cover layer 12 is also larger than that of the patch layer 13, and the cover layer 12 and the patch layer 13 are layered through the buffer material 17 and the shielding film 16 so that the cover adhesive 15 is left around the patch layer 13.

In this case, it is preferable that the size (area) of the cover layer 12 be 150 to 250% of a plane area of the patch layer 13, similarly to the first embodiment.

Similarly, in the patch preparation of the second embodiment, the buffer material 17, the shielding film 16, and the patch support 18 may be configured separately. Alternatively, the buffer material 17, the shielding film 16, and the patch support 18 may be configured to be integrated together, like the laminate support described below. A method of bonding the buffer material 17, the shielding film 16, and the patch support 18 may be either a dry lamination method or a thermal lamination method. The dry lamination method is preferable.

In the patch preparation of the present invention, the drug is added to the adhesive plaster constituting the patch layer.

The drug that can be added is not particularly limited, and it is preferable that the drug be a transdermally absorbable drug. Examples of such a drug may include topical anaesthetics (bupivacaine hydrochloride, mepivacaine hydrochloride, etc.), antiepileptics (sodium valproate, etc.), analgesics (morphine hydrochloride, fentanyl citrate, buprenorphine hydrochloride, etc.), antipyretic analgesics (sulpyrine, antipyrine, acetaminophen, etc.), antipsychotics (chloropromazine hydrochloride, levomepromazine hydrochloride, clocapramine hydrochloride, etc.), antidepressants (imipramine hydrochloride, trazodone hydrochloride, fluvoxamine maleate, etc.), antidementia agents (donepezil, rivastigmine, galantamine hydrobromide, memantine hydrochloride, etc.), antianxiety agents (diazepam, alprazolam, tandospirone citrate, etc.), tranquilizers (hydroxyzine hydrochloride, etc.), brain function activating agents (tiapride hydrochloride, protirelin tartrate, etc.), cerebral circulation activators (isosorbide, pentoxifylline, fasudil hydrochloride, etc.), anti-parkinsonean agents (benserazide hydrochloride, amantazine hydrochloride, talipexole hydrochloride, etc.), muscle relaxants (epirizone hydrochloride, tizanidine hydrochloride, tolperisone hydrochloride, etc.), antipeptic ulcer agents (scopolamine butyl bromide, pirenzepine hydrochloride, timepidium bromide, etc.), antihistamines (chlorophenylamine maleate, promethazine hydrochloride, cetirizine hydrochloride, etc.), chemical mediator release inhibitors (emedastin fumarate, suplatast tosylate, epinastin hydrochloride, etc.), cardiopathy therapeutics (aminophylline, diltiazem hydrochloride, nicorandil, propranolol hydrochloride, isoprenaline hydrochloride, disopyramide phosphate, procainamide hydrochloride, etc.), antihypertensives (captopril, enarapril maleate, amosulalol hydrochloride, prazosin hydrochloride, urapidil, clonidine hydrochloride, etc.), vasodilators (tolazoline hydrochloride, etc.), vasoconstrictors (ameziniummethyl sulfate, etilefrine hydrochloride, phenylefrine hydrochloride, midodrine hydrochloride, etc.), anti-hyperlipemic agents (pravastatine sodium, fluvastatin sodium, cerivastatin sodium, etc.), antitussive expectorants (dextromethorphan hydrobromide, fominoben hydrochloride, acetylcisteine, etc.), anti-asthmatic agents (clenbuterol hydrochloride, fenoterol hydrobromide, procaterol hydrochloride, etc.), $H_2$ blockers (ranitidine hydrochloride, roxadine acetate hydrochloride, etc.), proton pump inhibitors (omeprazole, lansoprazole, rabeprazole, etc.), antiemetics (granisetron hydrochloride, azasetrone hydrochloride, ondansetron hydrochloride, ramosetrone hydrochloride, etc.), nonsteroidal anti-inflammatory agents (loxoprofen sodium, flurbiprofen, diclofenac sodium, tiaramide hydrochloride, etc.), antirheumatic agents (bucillamine, penicillamine, etc.), urinary disease therapeutics (oxybutynin hydrochloride, tamsulosine hydrochloride, propiverine hydrochloride, etc.), and β-blockers (bisoprolol fumarate, betaxolol hydrochloride, etc.).

The amount of the drug to be mixed is varied depending on the kind thereof, and is 5 to 30% by weight, preferably 5 to 20% by weight, and more preferably 10 to 20% by weight, relative to the weight of the whole adhesive plaster.

In addition to the drug, the adhesive plaster can contain another ingredient such as a base.

As the base mixed in the adhesive plaster, a rubber-based polymer, an acrylic polymer, or a silicone-based polymer is preferably used.

Examples of the rubber-based polymer may include a styrene-isoprene-styrene block copolymer (hereinafter abbreviated as SIS), isoprene, polyisobutylene (hereinafter abbreviated as PIB), a styrene-butadiene-styrene block copolymer (hereinafter abbreviated as SBS), and a styrene-butadiene rubber (hereinafter abbreviated as SBR).

The acrylic polymer is not particularly limited as long as it is a copolymer containing at least one (meth)acrylic acid derivate represented by 2-ethylhexyl acrylate, methyl acrylate, butyl acrylate, hydroxyethyl acrylate, 2-ethylhexyl methacrylate, or the like.

Specific examples thereof to be used may include adhesives such as an acrylic acid-acrylic acid octyl ester copolymer, a 2-ethylhexyl acrylate-vinyl pyrrolidone copolymer solution, an acrylic acid ester-vinyl acetate copolymer, a 2-ethylhexyl acrylate-2-ethylhexyl methacrylate-dodecyl methacrylate copolymer, an emulsion of methyl acrylate-2-ethylhexyl acrylate copolymer, and an acrylic polymer contained in an acrylic resin alkanolamine solution, which are described in Iyakuhin tenkabutu jiten 2007 (edited by International Pharmaceutical Excipients Council Japan), DURO-TAK acrylic adhesive series (available from National Starch and Chemical Company), and EUDRAGIT series (available from HIGUCHI INC.).

Specific examples of the silicone-based polymer may include a silicone rubber such as polyorganosiloxane.

Two or more kinds of such hydrophobic polymer may be mixed and used. In consideration of formation of the adhesive plaster and sufficient permeability, the amount of the polymer to be mixed relative to the weight of the total composition is 5 to 90% by weight, preferably 10 to 80% by weight, and more preferably 10 to 50% by weight.

The adhesive plaster may contain an absorption promoter. Examples of the usable absorption promoters may include fatty acid esters, higher alcohols, and surfactants.

Specific examples thereof may include methyl laurate, hexyl laurate, triethyl citrate, isopropyl myristate, myristyl myristate, octyldodecyl myristate, cetyl palmitate, triacetin, cetyl lactate, lauryl lactate, methyl salicylate, glycol salicylate, ethylene glycol salicylate, diethyl sebacate, diisopropyl sebacate, middle-chain fatty acid triglyceride, lauryl alcohol, stearyl alcohol, isostearyl alcohol, myristyl alcohol, oleyl alcohol, cetanol, glycerol monocaprylate, glycerol monocaprate, glycerol monolaurate, glycerol monooleate, sorbitan monolaurate, sorbitan monooleate, sucrose monolaurate, Polysorbate 20, propylene glycol monolaurate, polyethylene glycol monolaurate, polyethylene glycol monostearate, lauromacrogol, HCO-60, lauric acid diethanolamide, N-methyl-2-pyrrolidone, crotamiton, and dimethylsulfoxide. Preferable examples thereof may include triethyl citrate, isopropyl myristate, cetyl lactate, oleyl alcohol, sorbitan monooleate, polyethylene glycol monostearate, lauromacrogol, N-methyl-2-pyrrolidone, and triacetin.

Two or more kinds of the absorption promoter may be used in combination.

In consideration of sufficient permeability of principal agent as the patch preparation, and skin irritation such as rubor and edema, it is preferable that the absorption promoter be mixed in an amount of about 0.01 to 20% by weight, preferably 0.05 to 10% by weight, and more preferably 1 to 10% by weight, relative to the weight of total composition of the adhesive plaster.

The adhesive plaster may contain a plasticizer. Examples of the usable plasticizer may include petroleum-based oils (for example, a paraffin-based process oil, a naphthene-based process oil, and an aromatic process oil), squalane, squalene, plant-based oils (for example, an olive oil, a camellia oil, a tall oil, a peanut oil, and a castor oil), silicone oils, dibasic acid esters (for example, dibutyl phthalate, and dioctyl phthalate), liquid rubbers (for example, polybutene, and liquid isoprene rubber), fatty acid esters (isopropyl myristate, hexyl laurate, diethyl sebacate, and diisopropyl sebacate), diethylene glycol, polyethylene glycol, propylene glycol, and dipropylene glycol. In particular, a liquid paraffin, a liquid polybutene, and a silicone oil are preferred.

Two or more kinds of the plasticizer may be mixed and used, and in consideration of sufficient skin permeability and maintenance of sufficient cohesive force as the patch preparation, the total amount of such plasticizers to be mixed relative to the total composition of the adhesive plaster is 10 to 70% by weight, preferably 10 to 60% by weight, and more preferably 10 to 50% by weight.

In order to adjust the adhesive force, a tackifying resin may be mixed in the adhesive plaster of the present invention. Examples of the usable tackifying resin may include rosin derivatives (for example, rosin, a rosin glycerol ester, hydrogenated rosin, a hydrogenated rosin glycerol ester, and a pentaerythritol ester of rosin), an alicyclic saturated hydrocarbon resin (for example, ARKON P100, available from Arakawa Chemical Industries, Ltd.), an aliphatic hydrocarbon resin (for example, Quinton B170, available from Zeon Corporation), a terpene resin (for example, Clearon P-125, available from YASUHARA CHEMICAL CO., LTD.), and a maleic acid resin.

In consideration of the sufficient adhesive force as the patch preparation and irritation to the skin during peeling, the amount of such a tackifying resin to be added relative to the total composition of the adhesive plaster can be 5 to 70% by weight, preferably 5 to 60% by weight, and more preferably from 10 to 50% by weight.

Further, the adhesive plaster may contain an antioxidant, a filler, a crosslinker, a preservative, and an ultraviolet absorber, if necessary.

It is desirable that the antioxidant be tocopherol or an ester derivative thereof, ascorbic acid, ascorbyl stearate, nordihydroguaiaretic acid, dibutylhydroxytoluene (hereinafter abbreviated as BHT), or butylated hydroxyanisole.

It is desirable that the filler be calcium carbonate, magnesium carbonate, a silicate salt (for example, aluminum silicate, and magnesium silicate), silicic acid, barium sulfate, calcium sulfate, calcium zincate, zinc oxide, or titanium oxide.

It is desirable that the crosslinker be a thermosetting resin such as an amino resin, a phenolic resin, an epoxy resin, an alkyd resin, and unsaturated polyester, an isocyanate compound, a blocked isocyanate compound, an organic crosslinker, or an inorganic crosslinker such as a metal or a metal compound.

It is desirable that the preservative be ethyl parahydroxybenzoate, propyl parahydroxybenzoate, or butyl parahydroxybenzoate.

It is desirable that the ultraviolet absorber be an ultraviolet absorber such as a p-aminobenzoic acid derivative, an anthranilic acid derivative, a salicylic acid derivative, an amino acid-based compound, a dioxane derivative, a coumarin derivative, an imidazoline derivative, and a pyrimidine derivative.

The antioxidant, filler, crosslinker, preservative, or ultraviolet absorber can be preferably mixed in an amount of 10% by weight or less, preferably 5% by weight or less, and particularly preferably 2% by weight or less relative to the weight of the total composition of the adhesive plaster.

As the patch support in the patch preparation of the present invention, a stretchable or non-stretchable support can be used. For example, the support is selected from a fabric, a non-woven fabric, films of polyurethane, polyester, polyvinyl acetate, polyvinylidene chloride, polyethylene, polyethylene terephthalate (hereinafter abbreviated as PET), and aluminum foil, and a composite material. A PET film is preferable. When the support is a film of PET or the like, it is preferable that the thickness thereof be 4 to 75 µm.

The patch preparation of the present invention has characteristics in which the buffer material is disposed between the patch layer and the cover layer. Such a buffer material is not limited as long as it has cushioning properties. Examples thereof may include a urethane sheet, a non-woven fabric, a rubber sponge, and a plastic foam. In particular, a non-woven fabric is preferable. When the buffer material is a non-woven fabric, it is preferable that the fabric weight thereof be about 30 to 150 $g/m^2$, and more preferably 50 to 100 $g/m^2$.

In the patch preparation of the present invention, the shielding film may be further provided between the buffer material disposed on the patch layer and the cover layer.

The shielding film is provided to enhance the adhesion of the cover layer and the patch layer including the buffer material. When the patch support is a highly permeable material such as a non-woven fabric or a woven fabric and the buffer material is a non-woven fabric, the shielding film has both an effect of preventing transfer of the adhesive ingredient contained in the cover adhesive into the adhesive plaster and an effect of preventing transfer of the ingredient of the adhesive plaster into the cover adhesive.

As the shielding film, a sheet-shaped product of polyurethane, polyester, polyvinyl acetate, polyvinylidene chloride, polyethylene, PET, or aluminum foil can be preferably used. In particular, PET is preferable.

It is preferable that the thickness of the shielding film be 4 to 75 µm.

The cover layer in the patch preparation of the present invention includes the cover support and the cover adhesive, and has an effect of firmly fixing the patch layer on the skin.

For example, a constituent material for the cover support is selected from a fabric, a non-woven fabric, films of polyurethane, polyester, polyvinyl acetate, polyvinylidene chloride, polyethylene, PET, and aluminum, and a composite material thereof. In particular, a non-woven fabric or PET is preferably used. When the material is a non-woven fabric, the non-woven fabric having a fabric weight of 30 to 150 $g/m^2$, and more preferably 50 to 100 $g/m^2$ is used.

A base ingredient used for the cover adhesive is not particularly limited as long as it is a biocompatible material capable of bonding the patch preparation to the skin. It is preferable that the base ingredient be a pressure-sensitive adhesive, and more preferably polyacrylate, polydimethyl siloxane, polyisobutylene, or a combination thereof. For example, a publicly known tackifier or the like may be further added to the constituent material for the adhesive layer.

The release liner is not particularly limited as long as it protects the adhesive plaster and prevents decomposition of the drug in the adhesive plaster until the patch preparation is applied to the skin, and it is silicon-coated so as to be easily peeled.

Specific examples thereof may include a polyethylene film, a polyethylene terephthalate film, and a polypropylene film that are silicon-coated.

Next, a method for producing the patch preparation provided by the present invention will be described.

A material constituting the adhesive plaster is first mixed in an appropriate organic solvent such as toluene to obtain a plaster solution. The plaster solution is applied onto the liner, and dried at about 60 to 100° C., to obtain the adhesive plaster. The adhesive plaster is laminated on a patch support/a buffer material (laminate support) that is produced by laminating in advance on a side of the patch support, to produce an intermediate preparation (adhesive plaster+laminate support).

Subsequently, the base ingredient used in the cover adhesive is mixed in an appropriate organic solvent such as toluene to obtain a mixed solution. The mixed solution is applied to a plastic sheet such as a PET film, dried at about 60 to 80° C., and laminated on the cover support such as a non-woven fabric, to obtain a cover layer raw fabric.

The obtained cover layer raw fabric is punched into a desired size, and the plastic sheet is peeled from the raw fabric. The cover layer raw fabric is laminated on the intermediate preparation on a side of the laminate support, to obtain the patch preparation.

The aforementioned production method is a specific production method, and various modification thereof can be made.

EXAMPLES

Hereinafter, the present invention will be specifically described with reference to Examples of the patch preparation of the present invention. However, the present invention is not limited to these Examples, and various modifications thereof can be made without departing from the technical idea of the present invention.

<Production of Patch Support/Buffer Material (Laminate Support) or Patch Support/Buffer Material/Shielding Film (Laminate Support)>

A laminate support having the following layered structure of a patch support/a buffer material or a laminate support having the following layered structure of a patch support/a buffer material/a shielding film was produced.

Laminate Support 1:

A laminate support 1 was produced by laminating a PET film (thickness: 12 μm) as a patch support and a non-woven fabric (fabric weight: 100 g/m$^2$) as a buffer material.

Laminate Support 2:

A laminate support 2 was produced by laminating a PET film (thickness: 12 μm) as a patch support, a non-woven fabric (fabric weight: 50 g/m$^2$) as a buffer material, and a PET film (thickness: 12 μm) as a shielding film, in this order.

Laminate Support 3:

A laminate support 3 was produced by laminating a PET film (thickness: 12 μm) as a patch support, a non-woven fabric (fabric weight: 100 g/m$^2$) as a buffer material, and a PET film (thickness: 12 μm) as a shielding film, in this order.

Laminate Support 4:

A laminate support 4 was produced by laminating a PET film (thickness: 4 μm) as a patch support, a non-woven fabric (fabric weight: 50 g/m$^2$) as a buffer material, and a PET film (thickness: 4 μm) as a shielding film, in this order.

Laminate Support 5:

A laminate support 5 was produced by laminating a PET film (thickness: 4 μm) as a patch support, a non-woven fabric (fabric weight: 100 g/m$^2$) as a buffer material, and a PET film (thickness: 4 μm) as a shielding film, in this order.

Laminate Support 6:

A laminate support 6 was produced by laminating a PET film (thickness: 16 μm) as a patch support, a non-woven fabric (fabric weight: 50 g/m$^2$) as a buffer material, and a PET film (thickness: 16 μm) as a shielding film, in this order.

Laminate Support 7:

A laminate support 7 was produced by laminating a PET film (thickness: 16 μm) as a patch support, a non-woven fabric (fabric weight: 100 g/m$^2$) as a buffer material, and a PET film (thickness: 16 μm) as a shielding film, in this order.

<Production of Cover Layer Raw Fabric>

A cover layer raw fabric was produced by applying a cover adhesive to a plastic sheet (PET film), removing the solvent by drying, and bonding the cover adhesive to a cover support.

Cover Layer Raw Fabric:

67 Parts of Duro-Tak (registered trademark) 87-4287 as a cover adhesive and 33 parts of EUDRAGIT E100 (registered trademark) were dissolved and mixed in toluene, the mixture was applied to a PET film, and the solvent was removed by drying. After that, the cover adhesive was bonded to a non-woven fabric (fabric weight: 80 g/m$^2$) as a cover support to produce a cover raw fabric.

<Preparation of Adhesive Plaster Solution>

An adhesive plaster solution containing a drug (donepezil) in accordance with a formulation of the following Table 1 was prepared.

TABLE 1

| Ingredient | Mixing amount (%) |
| --- | --- |
| SIS | 22 |
| Liquid paraffin | 27 |
| Hydrogenated rosin glycerol ester | 40 |
| Lauryl alcohol | 5 |
| BHT | 1 |
| Donepezil | 5 |
| Total | 100 |

Donepezil and lauryl alcohol were dissolved in advance in toluene, and the mixture was mixed with other ingredients that were dissolved in toluene, to prepare the adhesive plaster solution.

The amount of toluene to be added was 50 parts by weight relative to 100 parts by weight of the plaster ingredient.

Example 1

The adhesive plaster solution prepared in advance as described above was applied onto a release film (release liner), the solvent was removed by drying, and the adhesive plaster was bonded to the laminate support 1. The laminate was punched into a size of 61 mm×61 mm, to produce an intermediate preparation (patch layer+buffer material).

The cover layer raw fabric produced in advance as described above was separately punched into a size of 71 mm×71 mm, and the PET film was peeled from the raw fabric. The cover layer raw fabric was bonded to the intermediate preparation (patch layer+buffer material) produced by punching as described above, to obtain a patch preparation of Example 1.

Examples 2 to 7

In accordance with the method described in the above-described Example 1, the adhesive plaster solution prepared in advance was applied onto a release film (release liner), and the solvent was removed by drying. The adhesive plaster was bonded to the laminate support 2 (Example 2), the laminate support 3 (Example 3), the laminate support 4 (Example 4), the laminate support 5 (Example 5), the laminate support 6 (Example 6), or the laminate support 7

(Example 7). Each laminate was punched into a size of 61 mm×61 mm, to produce an intermediate preparation (patch layer+buffer material+shielding film).

Subsequently, the cover layer raw fabric produced in advance was punched into a size of 71 mm×71 mm, and the PET film was peeled from the raw fabric. The cover layer raw fabric was bonded to the intermediate preparation (patch layer+buffer material+shielding film) produced by punching as described above, to obtain a patch preparation of each of Examples 2 to 7.

Comparative Example 1: Patch in which Buffer Material was not Disposed

The adhesive plaster solution prepared in advance was applied onto a release film (release liner), a solvent was removed by drying, and the adhesive plaster was bonded to a PET film (thickness: 16 μm) as a patch support. The laminate was punched into a size of 61 mm×61 mm, to produce an intermediate preparation (PET film+plaster).

The cover layer raw fabric produced in advance was separately punched into a size of 71 mm×71 mm, and the release film was peeled from the raw fabric. The cover layer raw fabric was bonded to the intermediate preparation (PET film+plaster) produced by punching as described above, to obtain a patch preparation of Comparative Example 1.

Compositions and the like of the patches of Examples 1 to 7 and the patch of Comparative Example 1 as described above are summarized in Table 2.

Example 2) described below and BIOSKIN (artificial skin: available from BEAULAX, CO., LTD.) as an adherend by the following test procedure.

<Procedure>

A pressure receiving sensor with a diameter of 20 mm was mounted on BIOSKIN as an adherend. The preparation of each of Examples and Comparative Examples was applied so that the pressure receiving sensor was disposed at a central region as much as possible.

A dish with a diameter of 90 mm was placed on the preparation, and a weight of 500 g was left to stand so that a load (pressure) was uniformly applied.

A state in which the pressure was constant was maintained for ten seconds, and the load was released.

A decrease behavior and a converged value of the pressure were graphed, and comparison and evaluation were performed. A convergence point was confirmed by examination in advance, to be 6 minutes (480 seconds).

Comparative Example 2

As a patch preparation of Comparative Example 2, a commercially available buprenorphine-containing tape (Norspan tape: registered trademark, transdermal absorption-type therapeutic agent for persistent pain/HISAMITSU PHARMACEUTICAL CO., INC.) was used.

A comparative test was classified into the following tests, and investigated.

TABLE 2

| | Patch layer | | Buffer material | | | | Cover layer Cover support | |
| --- | --- | --- | --- | --- | --- | --- | --- | --- |
| | Patch support | | | Fabric | Shielding film | | | Fabric |
| | Compt. | Thickness (μm) | Compt. | weight (g/m²) | Compt. | Thickness (μm) | Compt. | weight (g/m²) |
| Example 1 | PET | 12 | Non-woven fabric | 100 | — | | Non-woven Fabric | 80 |
| Example 2 | PET | 12 | Non-woven fabric | 50 | PET | 12 | Non-woven fabric | 80 |
| Example 3 | PET | 12 | Non-woven fabric | 100 | PET | 12 | Non-woven fabric | 80 |
| Example 4 | PET | 4 | Non-woven fabric | 50 | PET | 4 | Non-woven fabric | 80 |
| Example 5 | PET | 4 | Non-woven fabric | 100 | PET | 4 | Non-woven fabric | 80 |
| Example 6 | PET | 16 | Non-woven fabric | 50 | PET | 16 | Non-woven fabric | 80 |
| Example 7 | PET | 16 | Non-woven fabric | 100 | PET | 16 | Non-woven fabric | 80 |
| Comparative Example 1 | PET | 16 | — | | — | | Non-woven fabric | 80 |

Test Example 1: Contact Pressure Measurement

The patch preparation of the present invention is a patch preparation of a layered structure comprising a patch layer including an adhesive plaster containing a drug and a patch support, and a cover layer, wherein a buffer material is disposed between the patch support and the cover layer. Thus, the pressure-bonding property of the adhesive plaster of the patch layer to a portion to be attached to the skin by the cover layer is improved.

For demonstration of the improvement, the contact pressure was measured using each of the patch preparations of Examples 1 to 7 and Comparative Example 1 and a commercially available patch preparation (Comparative Test Example 1-(1)

Comparison of contact pressures at which the non-woven fabric with a fabric weight of 50 g/m² and the non-woven fabric with a fabric weight of 100 g/m² were used as the buffer material.

For the patch preparations of Examples 2 and 3 and Comparative Example 1, the comparison was investigated.

Test Example 1-(2)-A

Comparison of contact pressures at which the thicknesses of the patch support and the shielding film were different (at which the non-woven fabric with a fabric weight of 50 g/m² was used as the buffer material).

For the patch preparations of Examples 4 and 6 and Comparative Examples 1 and 2, the comparison was investigated.

Test Example 1-(2)-B

Comparison of contact pressures at which the thicknesses of the patch support and the shielding film were different (at which the non-woven fabric with a fabric weight of 100 g/m² was used as the buffer material).

For the patch preparations of Examples 5 and 7 and Comparative Examples 1 and 2, the comparison was investigated.

Test Example 1-(3)

Comparison of contact pressures at which the shielding film was disposed or not.

For the patch preparations of Examples 1 and 3 and Comparative Example 1, the comparison was investigated.
<Results>

Results of each test are shown in FIGS. 3 to 6.

As confirmed from the results in the drawings, the contact pressure of each patch preparation of the present invention to an adherend is higher than that of each patch preparation of Comparative Examples.

Therefore, the patch preparation of the present invention exhibits high adhesion to the adherend, the adhesive plaster is pressure-bonded to a portion attached to the skin with a constant pressure against the movement of the skin caused by motion or the like, and stable drug release can be achieved.

Test Example 2: Patch Test

A placebo preparation in which the drug was not contained in the patch preparation of each of Examples 2 to 5 and Comparative Example 1 was prepared. The placebo preparation was attached to the upper arm in four adult subjects. 24 Hours after the attachment, an attachment state of the preparation (presence or absence of peeling and floating) was observed.
<Procedure>

The area (adhesion area) of the patch layer firmly adhered to the skin, excluding portions of peeling and floating, was determined. The adhesion ratio of the patch layer to the skin 24 hours after the attachment was calculated by the following equation.

Adhesion ratio to the skin=(adhesion area/area of patch layer)×100 Unit: (%)

<Results>

The results are shown in Table 3.

TABLE 3

| Subject | Example 2 (Placebo) | Example 3 (Placebo) | Example 4 (Placebo) | Example 5 (Placebo) | Com. Ex. 1 (Placebo) |
| --- | --- | --- | --- | --- | --- |
| A | 90 | 90 | 90 | 90 | 65 |
| B | 80 | 95 | 95 | 95 | 80 |
| C | 100 | 100 | 80 | 90 | 70 |
| D | 100 | 100 | 100 | 100 | 80 |
| Average (%) | 93 | 96 | 96 | 94 | 74 |

As shown in Table 3, the adhesion ratio to the skin of each patch preparation of the present invention is higher than that of each patch preparation of Comparative Examples.

INDUSTRIAL APPLICABILITY

According to the present invention, the patch preparation of the layered structure in which the cover layer is provided on the patch, and the buffer material is disposed between the patch support and the cover layer is provided. As a result, the pressure-bonding property of an adhesive plaster of the patch layer to a portion attached to a skin by the cover layer can be improved, and pressure-bonding of the adhesive plaster to the portion attached to the skin under a constant pressure can be achieved to enable stable drug release.

Therefore, the patch preparation has a great medical effect in which a constant blood level of the drug can be maintained for an extended period as a patch especially containing a systemically active drug.

The invention claimed is:

1. A patch preparation of a layered structure comprising a patch layer including an adhesive plaster containing a drug and a patch support, wherein said patch support is a film, and a cover layer in this order from a side attached to a skin, wherein a buffer material is disposed between the patch support of the patch layer and the cover layer, and
    the buffer material is directly laminated to a first surface of the film such that the adhesive plaster containing the drug is directly positioned on an opposite surface of the film, and
    the cover layer has a size covering an area beyond a peripheral edge of the patch layer.

2. The patch preparation according to claim 1, wherein a shielding film is further disposed between the cover layer and the buffer material.

3. The patch preparation according to claim 1, wherein the buffer material is a non-woven fabric.

4. The patch preparation according to claim 2, wherein the shielding film is a polyethylene terephthalate (PET) film.

5. The patch preparation according to claim 1, wherein the cover layer has a size of 150 to 250% of a plane area of the patch layer.

* * * * *